United States Patent
Toyota

(10) Patent No.: US 12,426,821 B2
(45) Date of Patent: Sep. 30, 2025

(54) ION-SELECTIVE ELECTRODE AND PRODUCTION METHOD THEREFOR

(71) Applicant: Panasonic Intellectual Property Management Co., Ltd., Osaka (JP)

(72) Inventor: Kei Toyota, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1009 days.

(21) Appl. No.: 17/512,626

(22) Filed: Oct. 27, 2021

(65) Prior Publication Data

US 2022/0160280 A1   May 26, 2022

(30) Foreign Application Priority Data

Nov. 25, 2020   (JP) .................. 2020-195433

(51) Int. Cl.
*A61B 5/268* (2021.01)
*A61B 5/145* (2006.01)

(52) U.S. Cl.
CPC .............. *A61B 5/268* (2021.01); *A61B 5/145* (2013.01)

(58) Field of Classification Search
CPC ................................. A61B 5/268; A61B 5/145
See application file for complete search history.

(56) References Cited

U.S. PATENT DOCUMENTS

| | | | |
|---|---|---|---|
| 2005/0164019 A1* | 7/2005 | Liu | C07F 7/1804 428/917 |
| 2008/0185288 A1 | 8/2008 | Yokokawa | |
| 2021/0238205 A1* | 8/2021 | Nakahata | C08L 21/00 |

FOREIGN PATENT DOCUMENTS

| | | |
|---|---|---|
| JP | 11-514750 | 12/1999 |
| JP | 2000-119284 | 4/2000 |
| JP | 2000-119291 | 4/2000 |
| JP | 2000-121602 | 4/2000 |
| JP | 2004-239626 | 8/2004 |
| JP | 2008-191058 | 8/2008 |
| JP | 2017-512310 | 5/2017 |

(Continued)

OTHER PUBLICATIONS

Arkles, Gelest Silane Coupling Agents. 2014; Version 3.0,1-73 (Year: 2014).*

(Continued)

*Primary Examiner* — Luan V Van
*Assistant Examiner* — Randall Lee Gamble, Jr.
(74) *Attorney, Agent, or Firm* — Wenderoth, Lind & Ponack, L.L.P.

(57) ABSTRACT

An ion-selective electrode includes: an ion-sensitive layer containing an ion-sensitive substance; and a solid, in which at least a part of a surface of the solid is coated with the ion-sensitive layer, the ion-sensitive substance has a crown ether structure formed of at least two or more repeating units represented by Formula (a):

$$—CR^1R^2—CR^3X—O— \quad (a)$$

where X is an organic group having an alkoxysilyl group at a terminal, $R^1$, $R^2$, and $R^3$ are each a hydrogen atom or a hydrocarbon group, and $R^1$ or $R^2$ may be bonded to X, and at least one of the alkoxysilyl groups of the crown ether structure reacts to be bonded to at least a part of the surface of the solid.

11 Claims, 7 Drawing Sheets

(56) References Cited

FOREIGN PATENT DOCUMENTS

| | | |
|---|---|---|
| WO | 98/09160 | 3/1998 |
| WO | 2015/134317 | 9/2015 |
| WO | 2019/208723 | 10/2019 |

OTHER PUBLICATIONS

Glab et al. Ion-selective Electrodes | Glass Electrodes. Reference Module in Chemistry, Molecular Sciences and Chemical Engineering, 2013, pp. 1-5 (Year: 2013).*

Inokuchi et al. Ion Selectivity of Crown Ethers Investigated by UV and IR Spectroscopy in a Cold Ion Trap. The Journal of Physical Chemistry, 2012; 116, 4057-4068 (Year: 2012).*

Yu et al. Development of new solid-phase microextraction fibers by sol-gel technology for the determination of organophosphorus pesticide multiresidues in food. Journal of Chromatography A, 2004; 1036, 104-111 (Year: 2004).*

Wu et al. Synthesis and characterization of highly conductive plasticized double core organic-inorganic hybrid electrolytes for lithium polymer batteries. Journal of Power Sources, 2013; 238, 265-273 (Year: 2013).*

Chinese Search Report dated Aug. 12, 2025, for related Chinese Patent Application No. 202111373061.9.

\* cited by examiner

FIG. 8

| | | | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|---|
| First compound | 3-glycidoxypropyl-methyldimethoxysilane | Parts by mas | 22.0 | 17.6 | 11.0 | 2.2 | 19.8 | 0.0 | 13.2 | 8.8 | 0.0 | 9.3 | 9.3 |
| | 3-glycidoxypropyl-trimethoxysilane | Parts by mas | 0.0 | 0.0 | 0.0 | 0.0 | 2.4 | 2.4 | 9.5 | 14.2 | 0.0 | 4.3 | 0.0 |
| | 3-glycidoxypropyl-methyldiethoxysilane | Parts by mas | 0.0 | 0.0 | 0.0 | 0.0 | 0.0 | 22.4 | 0.0 | 0.0 | 0.0 | 0.0 | 0.0 |
| | 8-glycidoxyoctyl-trimethoxysilane | Parts by mas | 0.0 | 0.0 | 0.0 | 0.0 | 0.0 | 0.0 | 0.0 | 0.0 | 27.6 | 0.0 | 5.5 |
| Second compound | Methyltrimethoxysilane | Parts by mas | 0.0 | 2.7 | 6.8 | 0.0 | 0.0 | 0.0 | 0.0 | 0.0 | 0.0 | 1.6 | 1.6 |
| | Dimethyldimethoxysilane | Parts by mas | 0.0 | 0.0 | 0.0 | 0.0 | 0.0 | 0.0 | 0.0 | 0.0 | 1.2 | 3.4 | 3.4 |
| | Cyclohexylmethyl-dimethoxysilane | Parts by mas | 0.0 | 0.0 | 0.0 | 17.0 | 0.0 | 0.0 | 0.0 | 0.0 | 0.0 | 0.0 | 0.0 |
| Alkali metal salt | Lithium perchlorate | Parts by mas | 0.0 | 0.0 | 0.0 | 0.0 | 0.0 | 0.0 | 0.0 | 0.0 | 0.0 | 0.0 | 0.0 |
| | Sodium trifluoroacetate | Parts by mas | 1.4 | 1.1 | 0.7 | 0.3 | 3.4 | 3.4 | 3.4 | 3.4 | 3.4 | 2.0 | 2.0 |
| | Potassium iodide | Parts by mas | 0.0 | 0.0 | 0.0 | 0.0 | 0.0 | 0.0 | 0.0 | 0.0 | 0.0 | 0.0 | 0.0 |
| Type of solid | | — | Copper plate | Copper plate | Copper plate | Copper plate | Copper plate | Copper plate | Copper plate | Copper plate | Copper plate | Copper plate | Copper plate |
| Proportion relating to molar number of second compound | | R1 | 0 | 0.2 | 0.5 | 0.9 | 0 | 0 | 0 | 0 | 0.1 | 0.4 | 0.4 |
| Proportion relating to molar number of alkoxy group | | R2 | 0 | 0.2 | 0.5 | 0 | 0.1 | 0.1 | 0.4 | 0.6 | 0.9 | 0.3 | 0.3 |
| Charact-eristics | Retention rate | % | 90 | 95 | 91 | 90 | 95 | 91 | 94 | 96 | 94 | 94 | 91 |
| | | Determination | A | A | A | A | A | A | A | A | A | A | A |
| | Potential response | mV/decade | 45.3 | 51.7 | 50.6 | 41 | 41.1 | 42 | 46.5 | 47.5 | 47.4 | 52.2 | 54 |
| | | Determination | B | A | A | B | B | B | B | B | B | A | A |
| | Elastic modulus | MPa | 97 | 123 | 214 | 102 | 109 | 108 | 115 | 360 | 447 | 207 | 252 |
| | | Determination | B | A | A | B | B | B | A | B | B | A | A |

FIG. 9

| | | | Example 12 | Example 13 | Example 14 | Example 15 | Example 16 | Example 17 | Example 18 | Example 19 | Example 20 | Example 21 | Comparative example 1 |
|---|---|---|---|---|---|---|---|---|---|---|---|---|---|
| First compound | 3-glycidoxypropyl-methyldimethoxysilane | Parts by mas | 4.4 | 17.6 | 17.6 | 9.3 | 9.3 | 22.0 | 22.0 | 1.1 | 1.1 | 10.2 | 0.0 |
| | 3-glycidoxypropyl-trimethoxysilane | Parts by mas | 0.0 | 0.0 | 0.0 | 4.3 | 4.3 | 0.0 | 0.0 | 0.0 | 22.4 | 0.0 | 0.0 |
| | 3-glycidoxypropyl-methyldiethoxysilane | Parts by mas | 0.0 | 0.0 | 0.0 | 0.0 | 0.0 | 0.0 | 0.0 | 0.0 | 0.0 | 0.0 | 0.0 |
| | 8-glycidoxyoctyl-trimethoxysilane | Parts by mas | 15.3 | 0.0 | 0.0 | 0.0 | 0.0 | 0.0 | 0.0 | 0.0 | 0.0 | 0.0 | 0.0 |
| Second compound | Methyltrimethoxysilane | Parts by mas | 0.0 | 2.7 | 2.7 | 1.6 | 1.6 | 0.0 | 0.0 | 0.0 | 0.0 | 0.0 | 0.0 |
| | Dimethyldimethoxysilane | Parts by mas | 1.8 | 0.0 | 0.0 | 3.4 | 3.4 | 0.0 | 0.0 | 11.4 | 0.0 | 0.0 | 0.0 |
| | Cyclohexylmethyl-dimethoxysilane | Parts by mas | 2.8 | 0.0 | 0.0 | 0.0 | 0.0 | 0.0 | 0.0 | 0.0 | 0.0 | 2.9 | 0.0 |
| Alkali metal salt | Lithium perchlorate | Parts by mas | 0.0 | 2.1 | 0.0 | 0.0 | 0.0 | 0.0 | 0.0 | 0.0 | 0.0 | 0.6 | 0.0 |
| | Sodium trifluoroacetate | Parts by mas | 1.0 | 0.0 | 0.0 | 0.8 | 0.4 | 1.4 | 1.4 | 0.2 | 3.4 | 0.0 | 0.0 |
| | Potassium iodide | Parts by mas | 0.0 | 0.0 | 3.3 | 0.0 | 0.0 | 0.0 | 0.0 | 0.0 | 0.0 | 0.0 | 0.0 |
| Type of solid | | | Copper plate | Copper plate | Copper plate | Copper plate | Copper plate | Glass container | Glassy carbon plate | Copper plate | Copper plate | Copper plate | — |
| Proportion relating to molar number of second compound | | R1 | 0.3 | 0.2 | 0.2 | 0.4 | 0.4 | 0 | 0 | 0.95 | 0 | 0.25 | — |
| Proportion relating to molar number of alkoxy group | | R2 | 0.5 | 0.2 | 0.2 | 0.3 | 0.3 | 0 | 0 | 0 | 0.95 | 0 | — |
| Characteristic | Retention rate | % | 92 | 92 | 93 | 91 | 95 | 93 | 95 | 90 | 85 | 92 | 83 |
| | | Determination | A | A | A | A | A | A | A | A | C | A | D |
| | Potential response | mV/decade | 55 | 50.1 | 50.5 | 54 | 52.3 | 49.7 | 43.2 | 39.1 | 41.2 | 51 | 52 |
| | | Determination | A | A | A | A | A | B | B | C | B | A | A |
| | Elastic modulus | MPa | 345 | 145 | 155 | 296 | 307 | 97 | 95 | 98 | 510 | 450 | — |
| | | Determination | A | A | A | A | A | B | B | B | C | B | — |

ION-SELECTIVE ELECTRODE AND PRODUCTION METHOD THEREFOR

BACKGROUND

1. Technical Field

The present disclosure relates to an ion-selective electrode and a production method therefor.

2. Description of the Related Art

In recent years, a new medical system based on constant monitoring of health conditions and biological information of a person has been constructed. In other words, it is a medical system that detects signs of problems in health conditions earlier in daily life and displays them, for example, on an information terminal, thereby preventing diseases or leading to early detection. In addition to its use in the medical system, monitoring human biological information and comfort and discomfort related to the five senses can provide useful information for a person to live more comfortably, which is beneficial to the lives of people and society as a whole.

Examples of a monitoring target of biological information including such health conditions include ions in a human body fluid. Although the body contains various ions, it is known that the ion concentration varies depending on health conditions. In order to constantly monitor ions in sweat, an ion-selective electrode that can be constantly brought into contact with human skin is required. An important component in determining the performance of an ion-selective electrode is an ion-sensitive membrane, which has the function of allowing only specific ions to pass through. As conventional ion-sensitive membranes, membranes formed by mixing an ion-sensitive substance, also called an ionophore, with a plasticizer in a membrane support are generally used.

Japanese Patent Unexamined Publication No. 2000-121602 proposes an ion-sensitive membrane obtained by bonding of an ion-sensitive substance having a crown ether derivative structure.

SUMMARY

One aspect of the present disclosure is an ion-selective electrode including: an ion-sensitive layer containing an ion-sensitive substance; and a solid, in which at least a part of a surface of the solid is coated with the ion-sensitive layer, the ion-sensitive substance has a crown ether structure formed of at least two or more repeating units represented by Formula (a):

$$-CR^1R^2-CR^3X-O- \qquad (a)$$

where X is an organic group having an alkoxysilyl group at a terminal, $R^1$, $R^2$, and $R^3$ are each a hydrogen atom or a hydrocarbon group, and $R^1$ or $R^2$ may be bonded to X, and at least one of the alkoxysilyl groups of the crown ether structure reacts to be bonded to at least a part of the surface of the solid.

Another aspect of the present disclosure is a production method for an ion-selective electrode, the method including: a step of preparing a solution obtained by dissolving an alkali metal salt or a salt of a group 2 element in a liquid containing a first compound having a epoxy group and an alkoxysilyl group at a terminal; a step of applying the solution to at least a part of a surface of a solid and leaving the solution to stand or heating the solution to coat at least a part of the surface of the solid; and a step of immersing the solid, of which at least a part of the surface is coated, in water, removing the water, and thereafter drying the solid.

BRIEF DESCRIPTION OF THE DRAWINGS

FIG. 8 is a table summarizing the results of Examples 1 to 11; and

FIG. 9 is a table summarizing the results of Examples 12 to 21 and Comparative Example 1.

DETAILED DESCRIPTIONS

Figure 1:
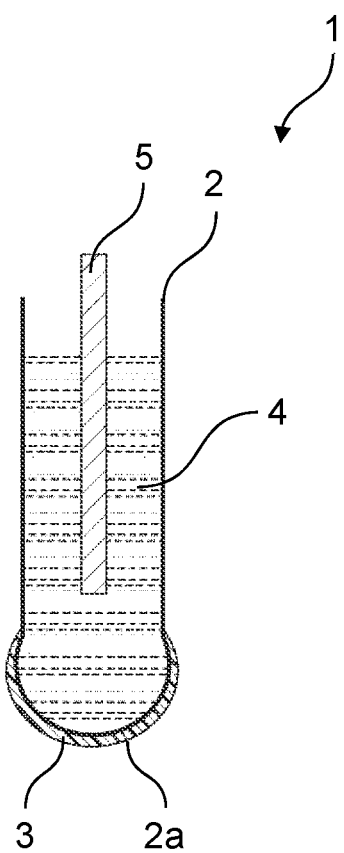
FIG. 1 is a schematic cross-sectional view of an ion-selective electrode in a case where a solid is a glass container.

It has been found that conventional ion-sensitive membranes may have insufficient durability when repeatedly used as an ion-selective electrode.

One of the objects of the present disclosure is to provide an ion-selective electrode exhibiting sufficient durability and a production method therefor.

Aspect 1 of the present disclosure is an ion-selective electrode including: an ion-sensitive layer containing an ion-sensitive substance; and a solid, in which at least a part of a surface of the solid is coated with the ion-sensitive layer, the ion-sensitive substance has a crown ether structure formed of at least two or more repeating units represented by Formula (a):

$$-CR^1R^2-CR^3X-O- \qquad (a)$$

where X is an organic group having an alkoxysilyl group at a terminal, $R^1$, $R^2$, and $R^3$ are each a hydrogen atom or a hydrocarbon group, and $R^1$ or $R^2$ may be bonded to X, and at least one of the alkoxysilyl groups of the crown ether structure reacts to be bonded to at least a part of the surface of the solid.

Aspect 2 of the present disclosure is the ion-selective electrode of Aspect 1, in which the crown ether structure may be a polymer containing a portion derived from a first compound having an epoxy group and an alkoxysilyl group at a terminal, and the polymer may be obtained by cyclically polymerizing the epoxy group by ring-opening with an alkali metal salt or a salt of a group 2 element.

Aspect 3 of the present disclosure is the ion-selective electrode of Aspect 2, in which a cation of the alkali metal salt or the salt of the group 2 element may be any of lithium ion, sodium ion, and potassium ion.

Aspect 4 of the present disclosure is the ion-selective electrode of any one of Aspects 1 to 3, in which in Formula (a), $R^1$, $R^2$, and $R^3$ may each be a hydrogen atom, and X may be represented by Formula (b):

$$\text{—CH}_2\text{O—Y} \tag{b}$$

where Y is a monovalent organic group having an alkoxysilyl group at a terminal.

Aspect 5 of the present disclosure is the ion-selective electrode of any one of Aspects 1 to 4, in which the number of repetitions of Formula (a) may be 10 or less.

Aspect 6 of the present disclosure is the ion-selective electrode of any one of Aspects 1 to 5, in which at least one of the alkoxysilyl groups of the crown ether structure may react to form a siloxane bond.

Aspect 7 of the present disclosure is the ion-selective electrode of any one of Aspects 1 to 6, in which the ion-sensitive layer may contain a portion derived from a second compound represented by Formula (c):

$$R^4\text{—Z} \tag{c}$$

where $R^4$ is a monovalent hydrocarbon group, and Z is a monovalent organic group having an alkoxysilyl group at a terminal.

Aspect 8 of the present disclosure is the ion-selective electrode of Aspect 7, in which a siloxane bond may be formed from a portion derived from the alkoxysilyl group in the crown ether structure and a portion derived from the alkoxysilyl group of the second compound.

Aspect 9 of the present disclosure is the ion-selective electrode of Aspect 7 or 8, in which a ratio of a molar number of a portion derived from the second compound to a sum of a molar number of a portion derived from a portion represented by Formula (a) and a molar number of a portion derived from the second compound may be 0.9 or less.

Aspect 10 of the present disclosure is the ion-selective electrode of any one of Aspects 7 to 9, in which a ratio of a sum of a molar number of a portion derived from a portion represented by Formula (a) in which the number of alkoxy groups in X of Formula (a) is 3 and a molar number of a portion derived from the second compound in which the number of alkoxy groups in Z of Formula (c) is 3 to a sum of a molar number of a portion derived from a portion represented by Formula (a) and a molar number of a portion derived from the second compound may be 0.9 or less.

Aspect 11 of the present disclosure is the ion-selective electrode of any one of Aspects 1 to 10, in which the solid may contain a conductive material.

Aspect 12 of the present disclosure is the ion-selective electrode of any one of Aspects 1 to 10, in which the solid may be a glass container, the surface of the solid may be an outer surface of the glass container, and the ion-selective electrode may further include: a conductive member so that the conductive member comes into contact with an electrolytic solution when the glass container is filled with the electrolytic solution.

Aspect 13 of the present disclosure is a production method for an ion-selective electrode, the method including: a step of preparing a solution obtained by dissolving an alkali metal salt or a salt of a group 2 element in a liquid containing a first compound having an epoxy group and an alkoxysilyl group at a terminal; a step of applying the solution to at least a part of a surface of a solid and leaving the solution to stand or heating the solution to coat at least a part of the surface of the solid; and a step of immersing the solid, of which at least a part of the surface is coated, in water, removing the water, and thereafter drying the solid.

Aspect 14 of the present disclosure is the production method of Aspect 13, further including: leaving the solution to stand or heating the solution before applying the solution to at least a part of the surface of the solid.

Aspect 15 of the present disclosure is the production method of Aspect 13 or 14, in which the solution further may contain a second compound represented by Formula (c):

$$R^4\text{—Z} \tag{c}$$

where $R^4$ is a monovalent hydrocarbon group, and Z is a monovalent organic group having an alkoxysilyl group at a terminal.

According to the above-mentioned aspects, it is possible to provide an ion-selective electrode exhibiting sufficient durability and a production method therefor.

Hereinafter, exemplary embodiments of the present disclosure will be described in detail.

An ion-selective electrode according to an exemplary embodiment of the present disclosure includes: an ion-sensitive layer containing an ion-sensitive substance; and a solid, in which at least a part of a surface of the solid is coated with the ion-sensitive layer, the ion-sensitive substance has a crown ether structure formed of at least two or more repeating units represented by Formula (a):

$$\text{—CR}^1\text{R}^2\text{—CR}^3\text{X—O—} \tag{a}$$

where X is an organic group having an alkoxysilyl group at a terminal, $R^1$, $R^2$, and $R^3$ are each a hydrogen atom or a hydrocarbon group, and $R^1$ or $R^2$ may be bonded to X, and at least one of the alkoxysilyl groups of the crown ether structure reacts to be bonded to the surface of the solid.

The ion-selective electrode as described above is a solid membrane type ion-selective electrode exhibiting ion selectivity by an ion-sensitive substance bonded to the surface.

The ion-sensitive substance bonded to the solid surface exhibits ion selectivity due to a portion where two carbon atoms and one oxygen atom are repeatedly bonded in this order in a cyclic manner (hereinafter simply referred to as "cyclic structure"). Furthermore, a plurality of organic groups having an alkoxysilyl group at the terminal are present as side chains extending from the cyclic structure, and at least one of the alkoxysilyl groups reacts to be bonded to the solid surface (for example, chemisorption). Specifically, for example, because the alkoxysilyl group at the terminal may be hydrolyzed to a silanol group, bonding to the OH group on the solid surface may be caused by a dehydration condensation reaction. In the ion-selective electrode, loss of the cyclic structure is unlikely to occur, and the ion-selective electrode is suitable for retaining ion selectivity.

$R^1$, $R^2$, and $R^3$ in the ion-sensitive substance may each be a hydrogen atom or an alkyl group having 1 to 3 carbon atoms. Alternatively, $R^1$ or $R^2$ may be bonded to X, for example, $R^2$ and $R^3$ may each be a hydrogen atom, and two C's in Formula (a) and $R^1$ and X may form a cyclohexane ring together.

In a preferred exemplary embodiment, the crown ether structure is a polymer containing a portion derived from a first compound having an epoxy group and an alkoxysilyl group at a terminal, and this polymer is obtained by cyclically polymerizing the epoxy group by ring-opening with an alkali metal salt or a salt of a group 2 element. Thereby, an ion-sensitive substance suitable for detecting the cation of the alkali metal salt or the salt of the group 2 element used for ring-opening of the epoxy group can be obtained. The cation of the alkali metal salt or the salt of the group 2 element is preferably any of lithium ion, sodium ion, and potassium ion. Thereby, an ion-sensitive substance suitable for detecting any of lithium ion, sodium ion, and potassium ion can be obtained.

The first compound having an epoxy group and an alkoxysilyl group at the terminal is represented by Formula (d):

$$G-Y \quad (d)$$

G may be a functional group having an epoxy group, and examples of the functional group having an epoxy group include a glycidoxy group and an epoxycyclohexyl group, and the glycidoxy group is suitably used from the viewpoint that a cyclic structure is easily obtained upon ring-opening polymerization.

Y is a monovalent organic group having an alkoxysilyl group at a terminal, and is further embodied by Formula (e):

$$C_nH_{2n-2m-4f}SiR^5{}_{3-g}(OR^6)_g \quad (e)$$

$R^5$ and $R^6$ may be each independently at each occurrence any of a methyl group, an ethyl group, a propyl group, a butyl group, an isopropyl group, a pentyl group, an isobutyl group, a hexyl group, a phenyl group, and a cyclohexyl group, and $R^5$ and $R^6$ may be the same as or different from each other. Among them, a methyl group and an ethyl group can be suitably used from the viewpoint that an alkoxysilyl group is easily hydrolyzed and easily bonded to the solid surface.

n may be an integer of 0 to 8. When n is 8 or less, it is preferable because then it is possible to inhibit the excessive increase in the hydrophobicity of the compound having an epoxy group and an alkoxysilyl group at the terminal and secure the solubility of an alkali metal salt or a salt of a group 2 element in a liquid of the compound. Furthermore, n is preferably 3 or more from the viewpoint that steric hindrance due to an alkoxy group ($OR^3$) bonded to a silicon (Si) atom can be inhibited by securing a distance to the Si atom in the ring-opening polymerization of epoxy groups. In the hydrocarbon represented by $C_nH_{2n-2m-4f}$, m is the sum of the number of double bonds and the number of ring structures in the hydrocarbon, and f is the number of triple bonds in the hydrocarbon. g is an integer of 1 to 3. The first compound may contain at least one or more kinds of the compound represented by Formula (d), or may be a mixture of two or more kinds thereof.

Examples of the first compound include 3-glycidoxypropyltrimethoxysilane, 3-glycidoxypropylmethyldimethoxysilane, 3-glycidoxypropyltriethoxysilane, 3-glycidoxypropylmethyldiethoxysilane, 2-(3,4-epoxycyclohexyl) trimethoxysilane, 2-(3,4-epoxycyclohexyl) methyldimethoxysilane, 2-(3,4-ep oxycyclohexyl) triethoxysilane, and 2-(3,4-epoxycyclohexyl) methyldiethoxysilane.

In a preferred exemplary embodiment, examples of the first compound include the compound in which, in Formula (a), $R^1$, $R^2$, and $R^3$ are each a hydrogen atom and X is represented by Formula (b):

$$-CH_2O-Y \quad (b)$$

where Y is a monovalent organic group having an alkoxysilyl group at a terminal. With such a structure, the cyclic structure is easily formed stably. Y in Formula (b) may be the same as Y in Formula (d).

The number of repetitions of Formula (a) is preferably 4 or more. Accordingly, a large number of alkoxy groups at the terminal (at least four or more) can be secured, and the loss of the cyclic structure can be further inhibited. On the other hand, the number of repetitions is preferably 10 or less, and more preferably 6 or less. Accordingly, the size of the crown ether structure formed can be set to a size suitable for detecting ions that are abundant in nature, such as sodium ions, potassium ions, and calcium ions. Furthermore, the number of repetitions is more preferably 6 or less, as it is particularly suitable for detecting important ions in a living body such as potassium ion and sodium ion.

Examples of the crown ether structure include compounds of Chemical Formulas 1 and 2.

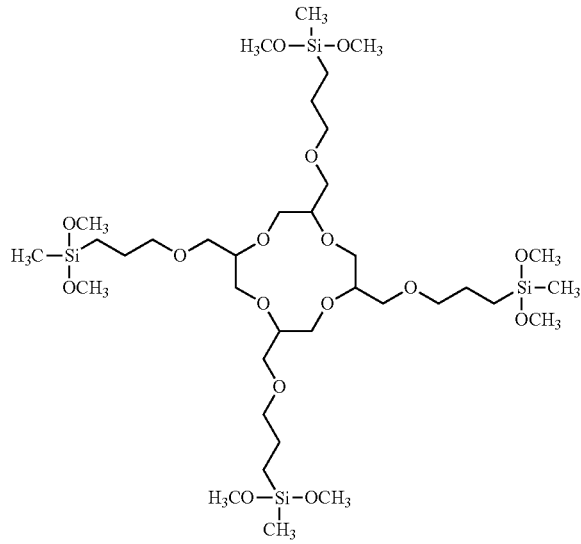

(Formula 1)

-continued

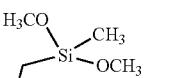
(Formula 2)

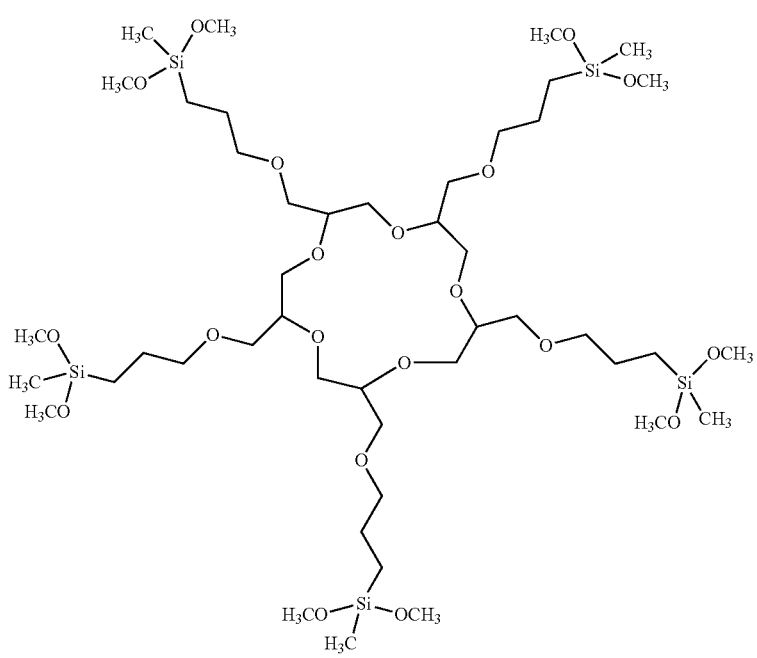

In the ion-sensitive layer containing the ion-sensitive substance, it is preferable that at least one of the alkoxysilyl groups (that is, X in Formula (a)) of the crown ether structure react (for example, at least one of the alkoxysilyl groups is hydrolyzed to form a silanol group, and a silanol group in one crown ether structure and a silanol group in another crown ether structure undergo a dehydration condensation reaction) to form a siloxane bond. Accordingly, loss of the cyclic structure is unlikely to occur, and ion selectivity can be further retained.

Furthermore, it is preferable that at least one of the alkoxysilyl groups contained in the crown ether structure react to form a siloxane bond, and at least one of the alkoxysilyl groups not forming the siloxane bond react to be bonded to the surface of the solid. Accordingly, loss of the cyclic structure is unlikely to occur, and ion selectivity can be further retained.

The ion-sensitive layer preferably contains a portion derived from a second compound represented by Formula (c):

(c)

where $R^4$ is a monovalent hydrocarbon group, and Z is a monovalent organic group having an alkoxysilyl group at a terminal). Accordingly, it is possible to obtain an ion-selective electrode that is chemically stable and has a long life due to the condition in which the hydrocarbon group $R^4$ does not show reactivity, as compared to the case in which the second compound is not contained. Furthermore, the density of the cyclic structure in the ion-sensitive layer can be controlled, making it possible to control a potential response to a desired response. Furthermore, by adjusting the number of alkoxy groups and/or hydrocarbon groups in the second compound, it is possible to adjust the elastic modulus of the ion-sensitive layer.

The "portion derived from the second compound" refers to a portion obtained by reaction of a part of the second compound and/or the alkoxysilyl groups of the second compound. The portion obtained by reaction of a part of the alkoxysilyl groups may be, for example, a portion obtained by hydrolysis of at least one of the alkoxysilyl groups to form a silanol group, and may be a portion obtained by the silanol group undergoing a dehydration condensation reaction with another silanol group, a hydroxyl (OH) group, or the like. The second compound may contain at least one or more kinds of the compound represented by Formula (c), or may be a mixture of two or more kinds thereof.

More specifically, Formula (c) can also be represented by Formula (f).

$$R^{41}_p R^{42}_q R^{43}_r Si(OR^7)_a(OR^8)_b(OR^9)_c \qquad (f)$$

$R^{41}$, $R^{42}$, and $R^{43}$ are no tparticularly limited, but can be, for example, a hydrocarbon group represented by General Formula $C_sH_{2s+1-2t-4u}$. s can be 1 or more and 20 or less. By setting s to 20 or less, it is possible to prevent excessively large steric hindrance and relatively easily form a siloxane bond. t is the sum of the number of double bonds and ring structures in the hydrocarbon group, and u is the number of triple bonds in the hydrocarbon group. $R^{41}$, $R^{42}$, and $R^{43}$ may all be the same as or different from each other.

Specific examples of $R^{41}$, $R^{42}$, and $R^{43}$ include a methyl group, an ethyl group, a propyl group, a butyl group, a hexyl group, a phenyl group, a cyclohexyl group, an octyl group, a decyl group, and an allyl group.

$R^7$, $R^8$, and $R^9$ may be a hydrocarbon group, and are preferably an alkyl group having 1 to 5 carbon atoms.

p, q, r, a, b, and c are integers of 0 or more which satisfy $1 \leq p+q+r \leq 3$, $1 \leq a+b+c \leq 3$, and $p+q+r+a+b+c=4$.

In the ion-sensitive layer, it is preferable that at least one of the alkoxysilyl groups of the second compound react to be bonded to the surface of the solid. Specifically, for example, because the alkoxysilyl group at the terminal of the second compound may be hydrolyzed to a silanol group, bonding to the OH group on the solid surface may be caused by a dehydration condensation reaction. Accordingly, it is possible to obtain an ion-selective electrode having a longer life.

In the ion-sensitive layer, a siloxane bond is preferably formed from a portion derived from the alkoxysilyl group in the crown ether structure and a portion derived from the alkoxysilyl group of the second compound. Accordingly, it is possible to obtain an ion-selective electrode having a longer life.

As a preferable proportion of a portion derived from the second compound, a ratio (hereinafter, may be referred to as "R1") of a molar number of a portion derived from the second compound to a sum of a molar number of a portion derived from a portion represented by Formula (a) and a molar number of a portion derived from the second compound is 0.9 or less. By setting R1 to 0.9 or less, the density of the cyclic structure in the ion-sensitive layer can be kept high, and the potential response can be increased. R1 is more preferably 0.5 or less. On the other hand, by increasing R1, a cyclic structure can be stably formed. R1 is 0 or more, preferably more than 0, and more preferably 0.2 or more. The "portion derived from the portion represented by Formula (a)" refers to a portion obtained by reaction of a portion represented by Formula (a) and/or a part of the alkoxysilyl groups in Formula (a). The portion obtained by reaction of a part of the alkoxysilyl groups may be, for example, a portion obtained by hydrolysis of at least one of the alkoxysilyl groups to form a silanol group, and may be a portion obtained by the silanol group undergoing a dehydration condensation reaction with another silanol group, a hydroxyl (OH) group, or the like. The portion represented by Formula (a) may be a portion obtained by ring-opening of the epoxy group of the first compound.

Furthermore, a ratio (hereinafter, may be referred to as "R2") of a sum of a molar number of a portion derived from a portion represented by Formula (a) in which the number of alkoxy groups in X of Formula (a) is 3 and a molar number of a portion derived from the second compound in which the number of alkoxy groups in Z of Formula (c) (that is, a+b+c in Formula (f)) is 3 to a sum of a molar number of a portion derived from a portion represented by Formula (a) and a molar number of a portion derived from the second compound is preferably 0 or more and 0.9 or less. Accordingly, it is possible to enhance the bondability to the solid surface (for example, chemisorption) while inhibiting cracks caused by volume shrinkage associated with the siloxane bond. R2 is more preferably 0.2 or more and 0.5 or less.

Furthermore, the number of alkoxy groups in X of Formula (a) is preferably 2 or 3, and the number of alkoxy groups in Z of Formula (c) is preferably 2 or 3. Accordingly, it is possible to enhance the bondability to the solid surface (for example, chemisorption) while inhibiting cracks caused by volume shrinkage associated with the siloxane bond.

The thickness of the ion-sensitive layer can be appropriately adjusted.

The solid preferably contains a conductive material. Accordingly, the ion-selective electrode can be constituted only by coating at least a part of the solid with the ion-sensitive layer. Examples of the conductive material include a metal material and a carbon material. The content of the conductive material is preferably 50% by mass or more with respect to the total weight of the solid. The solid is more preferably made of a conductive material, and the solid is even more preferably made of a metal material or a carbon material.

The metal material is not limited, and copper, silver, gold, platinum, iron, aluminum, zinc, nickel, and the like can be suitably selected from the viewpoint of general-purpose use, or the metal material may be an alloy such as stainless steel. As the carbon material, it is possible to use glassy carbon, graphite, diamond, amorphous carbon, and the like. Among them, glassy carbon can be suitably used from the viewpoint that it is required to detect a negative potential at the time of cation detection.

Furthermore, as the solid, a solid, which contains, for example, a glass material including silicon dioxide and the like, is likely to be bonded to the ion-sensitive layer and is preferable. Examples of the glass material include Pyrex (registered trademark), BK7, synthetic quartz, anhydrous synthetic quartz, soda-lime glass, and crystallized glass.

When a glass material is used as the solid, an ion-selective electrode as shown in FIG. 1 can be constituted. Ion-selective electrode 1 shown in FIG. 1 includes glass container 2 as a solid, in which the outer surface of bottom 2a of glass container 2 is coated with ion-sensitive layer 3, and ion-selective electrode 1 further includes conductive member 5 (for example, a conductive electrode) so that conductive member 5 comes into contact with electrolytic solution 4 when glass container 2 is filled with electrolytic solution 4. The depth of inserting conductive member 5 into glass container 2 is not particularly limited, but it is preferably 0.1 times or more and less than 1.0 times the depth of glass container 2, for example. Accordingly, it becomes easier for conductive member 5 to come into contact with electrolytic solution 4. Furthermore, it is preferable to provide a lid on the upper part of glass container 2 so that electrolytic solution 4 does not leak to the outside, and it is preferable that conductive member 5 be inserted into glass container 2 through the lid. In FIG. 1, the outer surface of bottom 2a of glass container 2 is coated with ion-sensitive layer 3, but coating is not limited to the outer surface of bottom 2a, and at least a part of the outer surface of glass container 2 may be coated with ion-sensitive layer 3. Furthermore, although bottom 2a of glass container 2 is spherical in FIG. 1, the bottom may have another shape.

The thickness of the portion (bottom 2a in FIG. 1) in glass container 2 coated with ion-sensitive layer 3 can be 100 μm or more and 1000 μm or less. By setting the thickness to 100 μm or more, the strength of glass container 2 can be secured, and breakage can be prevented. On the other hand, when the thickness is 1000 μm or less, the potential change when an ion to be measured is supplemented with an ion-sensitive substance can be easily propagated to electrolytic solution 4 in glass container 2, and the accuracy of potential measurement can be improved. The thickness of the portion coated with ion-sensitive layer 3 is more preferably 150 μm or more and 300 μm or less.

The ion-sensitive layer may coat at least a part of the surface of the solid, or may coat the entire surface of the solid depending on the constitution of the ion-selective electrode.

To the extent that the object of the exemplary embodiment of the present disclosure is achieved, the ion-selective electrode according to the exemplary embodiment of the present disclosure may contain other components.

Production Method for Ion-Selective Electrode

A production method for an ion-selective electrode according to an exemplary embodiment of the present disclosure includes step (A) of preparing a solution obtained by dissolving an alkali metal salt or a salt of a group 2 element in a liquid containing a first compound having an epoxy group and an alkoxysilyl group at a terminal; step (B) of applying the solution to at least a part of a surface of a solid and leaving the solution to stand or heating the solution to coat at least a part of the surface of the solid; and step (C)

of immersing the solid, of which at least a part of the surface is coated, in water, removing the water, and thereafter drying the solid.

Each of the steps will be described below.

Step (A) of Preparing Solution

A solution, which is obtained by dissolving an alkali metal salt or a salt of a group 2 element in a liquid containing a first compound (that is, the compound represented by Formula (d)) having an epoxy group and an alkoxysilyl group at a terminal, is prepared. The first compound can contain at least one or more kinds of the compound represented by Formula (d), or may be a mixture of two or more kinds thereof.

The alkali metal salt or the salt of the group 2 element in step (A) is not particularly limited, but is composed of a combination of a cation of the alkali metal or the group 2 element and an anion. Examples of the cation include lithium ion, sodium ion, potassium ion, magnesium ion, calcium ion, and strontium ion. Examples of the anion include chloride ion, bromide ion, iodide ion, perchlorate ion, thiocyanate ion, tetrafluoroborate ion, trifluoroacetate ion, nitrate ion, sulfate ion, hexafluoroarsenate ion ($AsF_6^-$), and hexafluorophosphate ion ($PF_6^-$). Among them, lithium salts, sodium salts, and potassium salts are preferable from the viewpoint of a high electron-withdrawing property and easy induction of ring-opening polymerization of an epoxy group, and lithium perchlorate, sodium trifluoroacetate, and potassium iodide are preferable from the viewpoint of higher solubility in the first compound.

Regarding the addition amount of the alkali metal salt or the salt of the group 2 element in step (A), a ratio (hereinafter referred to as "R3") of the molar number of the alkali metal salt or the salt of the group 2 element to the molar number of the first compound is preferably 0.05 or more. Accordingly, ring opening of the epoxy group of the first compound can be sufficiently promoted. Furthermore, a ratio (hereinafter referred to as "R4") of the molar number of the alkali metal salt or the salt of the group 2 element to the sum of the molar number of the first compound and the molar number of the second compound to be described later is preferably 0.25 or less. By setting R4 to 0.25 or less, it is possible to inhibit the alkali metal salt or the salt of the group 2 element from precipitating in a mixed liquid of the first compound and the second compound and to make the solution a homogeneous solution.

In step (A), an anion eliminating agent may be added to the solution. As the anion eliminating agent, known ones such as tetraphenylborate, sodium salt (DOJINDO LABORATORIES, Kalibor (registered trademark) (Na-TPB)), tetrakis[3,5-bis(trifluoromethyl)phenyl]borate, and sodium salt (DOJINDO LABORATORIES, T037 TFPB) can be used.

Step (B) of Applying Solution to at Least Part of Surface of Solid and Leaving Solution to Stand or Heating Solution to Coat at Least Part of Surface of Solid The solution is applied to at least a part of the surface of the solid and left to stand or heated to coat at least a part of the surface of the solid. By leaving the solution to stand or heating the solution, the epoxy group of the first compound is cyclically polymerized by ring-opening by the metal cation of the alkali metal salt or the salt of the group 2 element to form a crown ether structure. Furthermore, in the solution, an alkali metal ion or a group 2 element ion can be supported by a coordination bond from an oxygen atom in the crown ether structure. Furthermore, at least one of the alkoxysilyl groups of the crown ether structure may react to be bonded to the solid surface, or at least one of the alkoxysilyl groups of the second compound to be described later may react to be bonded to the solid surface. Specifically, for example, because the alkoxysilyl group may be hydrolyzed to a silanol group, bonding to a hydroxyl group (OH group) on the solid surface may be caused by a dehydration condensation reaction. Furthermore, the hydrolysis of the alkoxysilyl group at the terminal of the first compound and/or the second compound may proceed, and a dehydration condensation reaction may further proceed to allow the formation of a siloxane bond to proceed.

As an application method, it is possible to appropriately apply by a method such as immersion of the solid surface in the solution, dropwise addition of the solution onto the solid surface, spin coating, die coating, and spray spraying.

Furthermore, it is preferable to leave the solution to stand or heat the solution before applying the solution to at least a part of the solid surface (hereinafter, may be referred to as "first standing or heating"). That is, it is preferable to further include the first standing or heating separately from standing or heating after application to at least a part of the solid surface (hereinafter, may be referred to as "second standing or heating"). Accordingly, before application, the epoxy group of the first compound is cyclically polymerized by ring-opening by the metal cation of the alkali metal salt or the salt of the group 2 element to form a crown ether structure, and furthermore, in the solution, since hydrolysis of the alkoxysilyl group at the terminal of the first compound and the like may proceed, and a dehydration condensation reaction may further proceed to form a siloxane bond, the solution becomes highly viscous and easy to apply.

The time for the first standing or heating is preferably 20 minutes or longer. The time is more preferably 30 minutes or longer, 1 hour or longer, 24 hours or longer, 100 hours or longer, 500 hours or longer, and 720 hours or longer. The time for the second standing or heating is preferably 8 hours or longer and more preferably 24 hours or longer. This allows the ring-opening polymerization reaction of epoxy groups to proceed, thus yielding more ion-sensitive substances. Furthermore, the hydrolysis and dehydration condensation reaction of the alkoxysilyl group at the terminal following the ring-opening polymerization reaction of the epoxy group can be promoted.

The temperature for the first standing or heating and the temperature for the second standing or heating are preferably 20° C. or higher. Furthermore, the ring-opening polymerization reaction of the epoxy group and the subsequent hydrolysis and dehydration condensation reaction of the alkoxysilyl group at the terminal can proceed in a shorter time by increasing the temperature, and the temperature is more preferably 23° C. or higher or 40° C. or higher. The humidity of step (B) is not particularly limited, and in order to promote the hydrolysis, it is preferable that the moisture be in an environment such as an air atmosphere (that is, more than 0% RH).

It is preferable to add the second compound represented by Formula (c) to the above-mentioned solution. Accordingly, the ion-sensitive layer and the ion-selective electrode to be described later can become chemically stable and have a long life. The second compound can contain at least one or more kinds of the compound represented by Formula (c), or may be a mixture of two or more kinds thereof.

As the addition amount of the second compound, the ratio (that is, R1) of the molar number of the second compound to the sum of the molar number of the first compound and the molar number of the second compound is preferably 0.9 or less. By setting the ratio to 0.9 or less, the density of the cyclic structure in the ion-sensitive layer can be kept high, and the potential response can be increased. The ratio is more preferably 0.5 or less. On the other hand, by increasing R1, it is possible to inhibit linear polymerization at the time of the ring-opening polymerization of epoxy groups. R1 is 0 or more, preferably more than 0, and more preferably 0.2 or more.

Furthermore, each of the first compound and the second compound may have 1 to 3 alkoxy groups at the terminals. At this time, as a preferable proportion of the alkoxy groups, a ratio (that is, R2) of the sum of the molar number of the first compound having 3 alkoxy groups and the molar number of the second compound having 3 alkoxy groups to the sum of the molar number of the first compound and the molar number of the second compound is 0 or more and 0.9 or less. Accordingly, it is possible to enhance the bondability to the solid surface (for example, chemisorption) while inhibiting cracks caused by volume shrinkage associated with the siloxane bond. R2 is more preferably 0.2 or more and 0.5 or less.

Furthermore, the number of alkoxy groups in the first compound is preferably 2 or 3, and the number of alkoxy groups in the second compound is preferably 2 or 3. Accordingly, it is possible to enhance the bondability to the solid surface (for example, chemisorption) while inhibiting cracks caused by volume shrinkage associated with the siloxane bond.

Step (C) of Immersing Solid, of which at Least Part of Surface is Coated, in Water, Removing Water, and Thereafter Drying Solid After the step (B), an alkali metal ion or a group 2 element ion can be supported by a coordination bond from an oxygen atom in the crown ether structure. Therefore, after immersing the solid in a polar solvent such as water, the polar solvent such as water is removed, and then the solid is dried by air drying or the like. Accordingly, alkali metal ions or group 2 element ions are eluted in the polar solvent such as water and removed. The water is not particularly limited, and may be, for example, ion-exchanged water, ultrafiltered water, or distilled water.

The immersion time is preferably 24 hours or longer because then the ionic component can be sufficiently eluted.

When a glass material is used as the solid, a step for constituting the ion-selective electrode as shown in FIG. 1 (that is, a step of disposing conductive member 5, and the like) may be further included.

To the extent that the object of the exemplary embodiment of the present disclosure is achieved, the production method for the ion-selective electrode according to the exemplary embodiment of the present disclosure may include other steps.

EXAMPLES

Hereinafter, the exemplary embodiments of the present disclosure will be described in more detail with reference to examples. The exemplary embodiments of the present disclosure are not limited by the following examples, and can be implemented with appropriate modifications within the scope that can conform to the spirit described above and below, and all of them are included in the technical scope of the exemplary embodiments of the present disclosure.

Example 1

As a liquid of the first compound having an epoxy group and an alkoxysilyl group at the terminal, 22.0 parts by mass of 3-glycidoxypropylmethyldimethoxysilane (manufactured by Shin-Etsu Chemical Co., Ltd., KBM402, number of alkoxy groups: 2) was prepared. To 3-glycidoxypropylmethyldimethoxysilane, 1.4 parts by mass of sodium trifluoroacetate as an alkali metal salt was added and dissolved therein to prepare a solution.

A container containing the solution was put in a constant-temperature tank at 80° C. and heated for 24 hours as first standing or heating. The solution was added dropwise so as to be applied to the entire surface of a portion of a copper plate (length: 50 mm, width: 5 mm, thickness: 0.3 mm) from one end to 40 mm in a length direction. A portion 5 mm from the other end in a length direction (that is, the unapplied portion) was sandwiched by a clip and hanged in a constant-temperature tank at 80° C. to be heated for 24 hours as second standing or heating. Thereafter, the copper plate was immersed in ion-exchanged water for 24 hours. Thereafter, the ion-exchanged water was removed and air-dried to obtain an ion-selective electrode of Example 1.

Figure 2A:
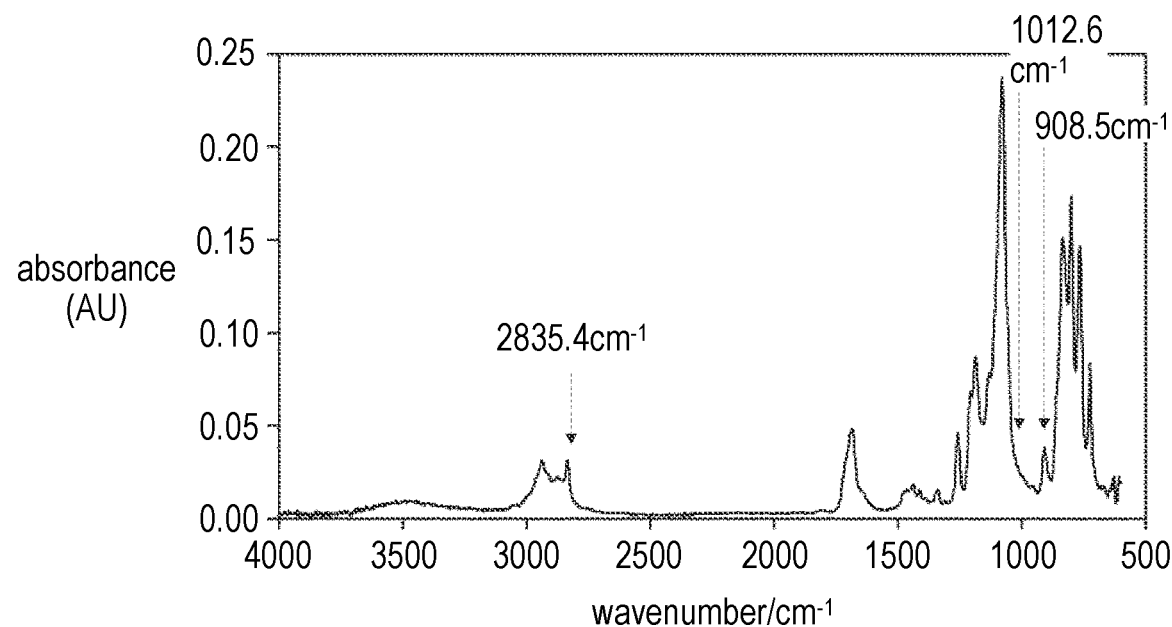
FIG. 2A is an attenuated total reflection FTIR spectrum of a solution before first standing or heating of Example 1.
Figure 2B:
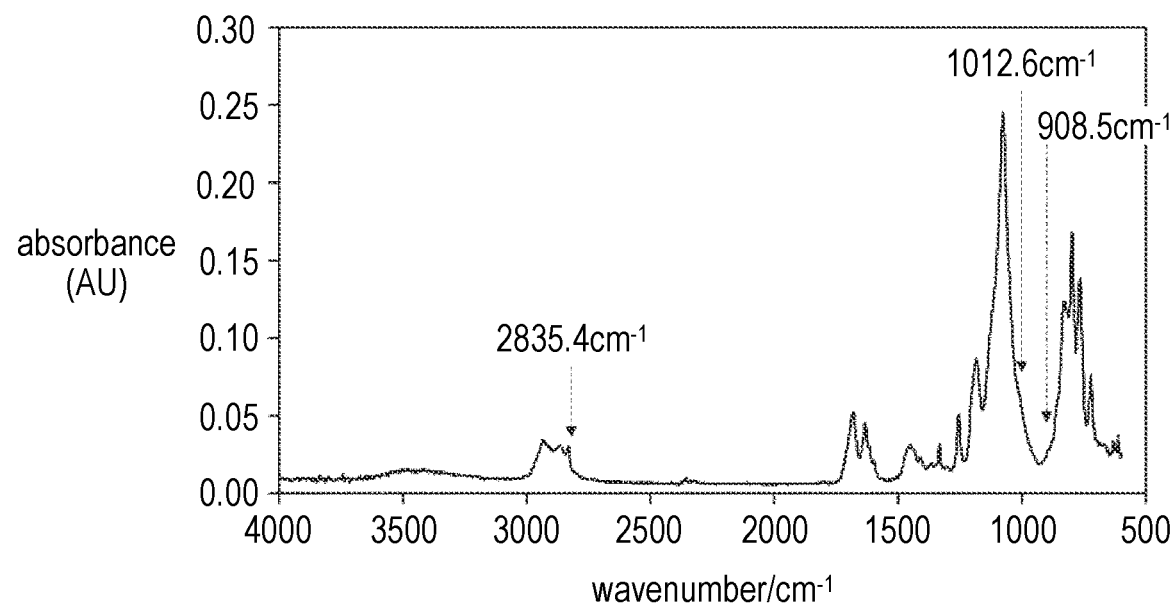
FIG. 2B is an attenuated total reflection FTIR spectrum of an ion-sensitive layer of Example 1.

In order to analyze the solution before the first standing or heating and the structure of the ion-sensitive layer formed on the solid surface of Example 1, the attenuated total reflection FTIR spectrum was measured (Shimadzu Corporation, IRPrestige-21). FIG. 2A is an attenuated total reflection FTIR spectrum of the solution of Example 1, and FIG. 2B is an attenuated total reflection FTIR spectrum of the ion-sensitive layer of Example 1. In FIG. 2A, the peak of 908.5 $cm^{-1}$ characteristic of an epoxy group and the peak of 2835.4 $cm^{-1}$ characteristic of a methoxy group are observed, whereas in FIG. 2B, these peaks are not confirmed or are greatly reduced. Furthermore, in FIG. 2A, the peak of 1012.6 $cm^{-1}$ derived from a siloxane bond is not observed, whereas in FIG. 2B, the shoulder peak is confirmed at 1012.6 $cm^{-1}$. Based on the above results, it was found that the ring-opening reaction of the epoxy group and at least the hydrolysis of the methoxy group proceeded in the ion-sensitive layer, and it is thought that the siloxane bond formation by the dehydration condensation reaction following the hydrolysis also proceeded.

Figure 3:
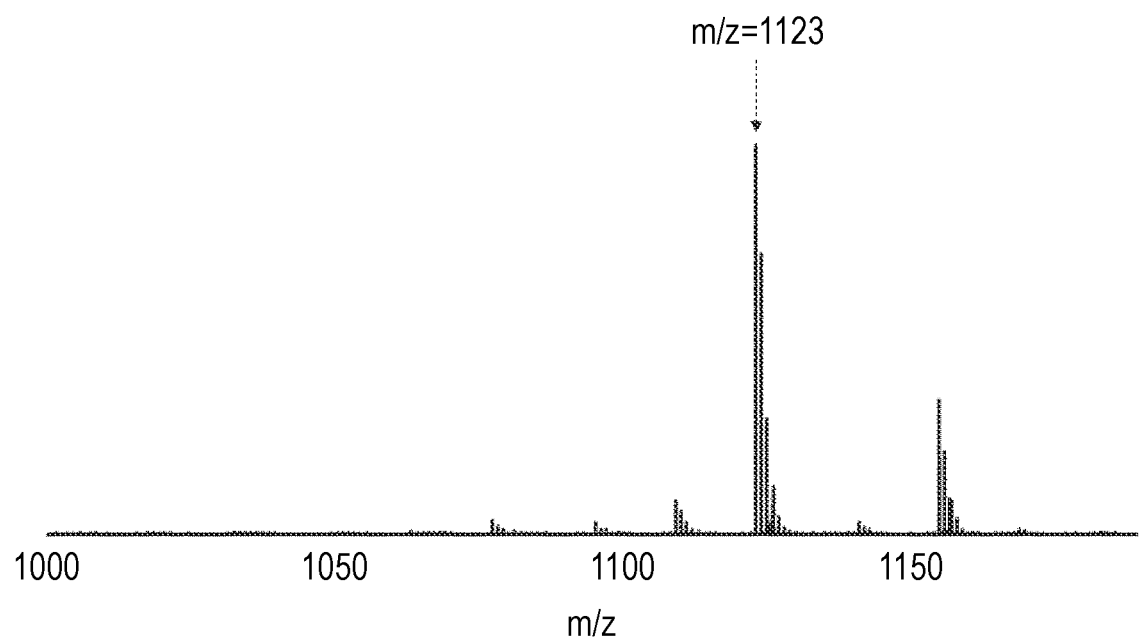
FIG. 3 is an MALDI-MS spectrum of a solution after first standing or heating of Example 1.

Matrix-assisted laser desorption/ionization mass spectrometry (hereinafter, MALDI-MS) spectra were measured (JEOL, JMS-S3000) for the solution after the first standing or heating of Example 1. The results are shown in FIG. 3. In FIG. 3, the peak of m/z=1123 was detected. It is thought that this is due to the structure in which sodium ions are supported on the polymer represented by Chemical Formula 2.

In Examples 2 to 21, ion-selective electrodes were produced by changing the type and addition amount of the first compound, the type and addition amount of the second compound, the type and addition amount of the alkali metal salt, and the type of solid from Example 1. In Examples 2 to 21, as the first compound, in addition to 3-glycidoxypropylmethyldimethoxysilane, 3-glycidoxypropyltrimethoxysilane (manufactured by Shin-Etsu Chemical Co., Ltd., KBM-403, number of alkoxy groups: 3), 3-glycidoxypropylmethyldiethoxysilane (number of alkoxy groups: 2), and 8-glycidoxyoctyltrimethoxysilane (manufactured by Shin-Etsu Chemical Co., Ltd., KBM-4803, number of alkoxy groups: 3) were used. As the second compound, methyltrimethoxysilane (manufactured by Shin-Etsu Chemical Co., Ltd., KBM-13, number of alkoxy groups: 3), dimethyldimethoxysilane (manufactured by Shin-Etsu Chemical Co., Ltd., KBM22, number of alkoxy groups: 2), and cyclohexylmethyldimethoxysilane (number of alkoxy groups: 2) were used. As the alkali metal salt, in addition to lithium perchlorate, sodium trifluoroacetate (manufactured by Kanto Chemical Co., Inc.), potassium iodide (manufactured by Kanto Chemical Co., Inc.) and the like were used. For those containing the second compound, after the first standing or heating, the second compound was added before application, and the container was manually shaken to stir and mix. For Examples 2 to 16 and 18 to 21 in which a copper plate and a glassy carbon plate were used as solids, the solution was applied to the solid in the same manner as in Example 1, and for Example 17 in which a glass container (thickness of bottom: 300 µm) was used as a solid, the solution was added dropwise to the bottom of the glass container and spread by hand almost uniformly while moving the glass container using interfacial tension. The procedure was performed in the same manner as Example 1 except that the unapplied portion of the glass container was sandwiched by a clip and hanged in a constant-temperature tank at 80° C. to be heated for 24 hours.

In Comparative Example 1, one obtained by mixing with a support PVC with bis[(12-crown-4)methyl]2-dodecyl-2-methylmalonate as an ion-sensitive substance (hereinafter referred to as "ion-sensitive membrane of Comparative Example 1") was used. As a production method for the ion-sensitive membrane of Comparative Example 1, 101 parts by mass of PVC having an average degree of polymerization of 1100 was dissolved in 3 ml of tetrahydrofuran (manufactured by Kanto Chemical Co., Ltd.), and 200 parts by mass of 2-nitrophenyl octyl ether (manufactured by FUJIFILM Wako Pure Chemical Corporation) was further added as a plasticizer and dissolved with 10 parts by mass of bis[(12-crown-4)methyl]2-dodecyl-2-methylmalonate (manufactured by FUJIFILM Wako Pure Chemical Corporation). This solution was added dropwise onto a petri dish and dried at room temperature for 24 hours.

Figure 4:
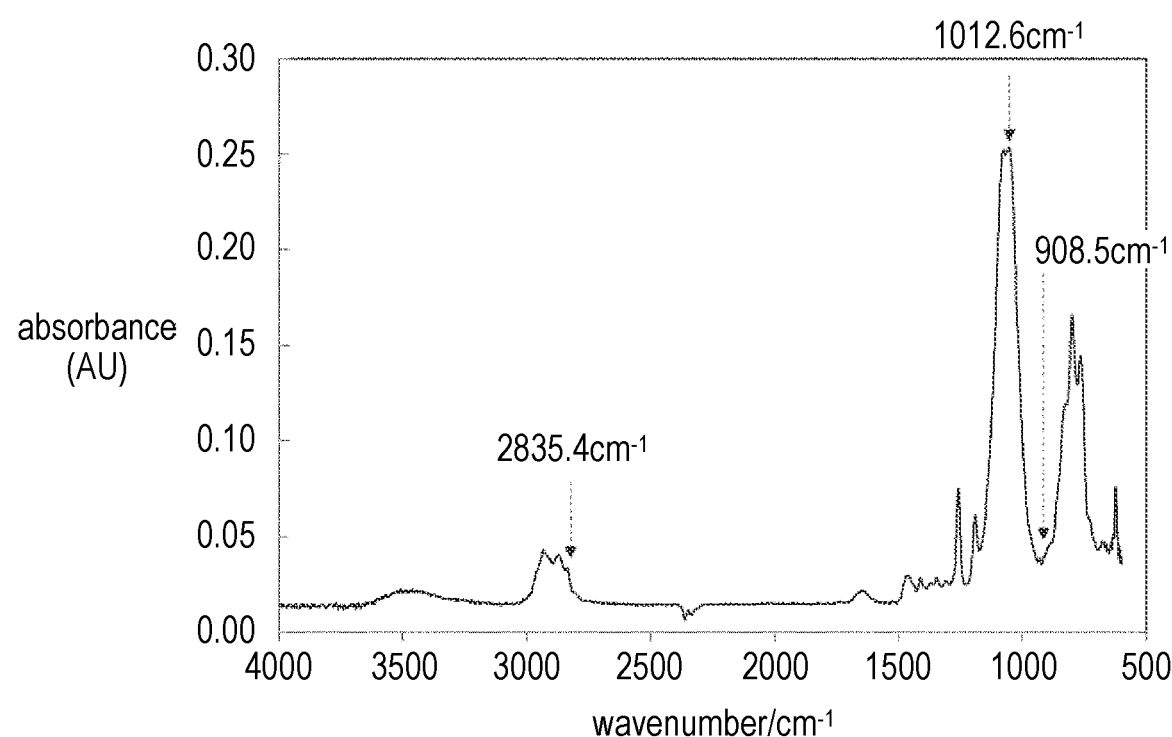
FIG. 4 is an attenuated total reflection FTIR spectrum of an ion-sensitive layer of Example 21.

FIG. 4 shows an attenuated total reflection FTIR spectrum of an ion-sensitive layer of Example 21. In Example 21, cyclohexylmethyldimethoxysilane (number of alkoxy groups: 2) was added as the second compound. In Example 21, similar to the attenuated total reflection FTIR of the ion-sensitive layer in Example 1, the peak of 908.5 $cm^{-1}$ characteristic of an epoxy group and the peak of 2835.4 $cm^{-1}$ characteristic of a methoxy group were not confirmed or were greatly reduced. Furthermore, a clear peak characteristic of a siloxane bond was confirmed at 1012.6 $cm^{-1}$. Based on these results, in the ion-sensitive layer of Example 21, it is thought that a siloxane bond is formed from a portion derived from the alkoxysilyl group in the crown ether structure and a portion derived from the alkoxysilyl group of the second compound.

MALDI-MS measurement was performed in the same manner as in Example 1 for the solution after the first standing or heating of Examples 2 to 21. In the case in which lithium perchlorate was used as the alkali metal salt (Examples 13 and 21), the peak caused by cyclic polymerization of the epoxy group of the first compound into four rings by ring-opening, and the structure in which lithium ions were supported was detected. In the case in which sodium trifluoroacetate was used as the alkali metal salt (Examples 1 to 12 and 15 to 20), the peak caused by cyclic polymerization of the epoxy group of the first compound into five rings by ring-opening, and the structure in which sodium ions were supported was detected. In the case in which potassium iodide was used as the alkali metal salt (Example 14), the peak caused by cyclic polymerization of the epoxy group of the first compound into six rings by ring-opening, and the structure in which potassium ions were supported was detected.

The potential response, durability against repeated use (hereinafter referred to as "retention rate"), and elastic modulus of the ion-selective electrodes obtained by each of the examples and the comparative example were evaluated.

Potential Response and Retention Rate

Figure 5:
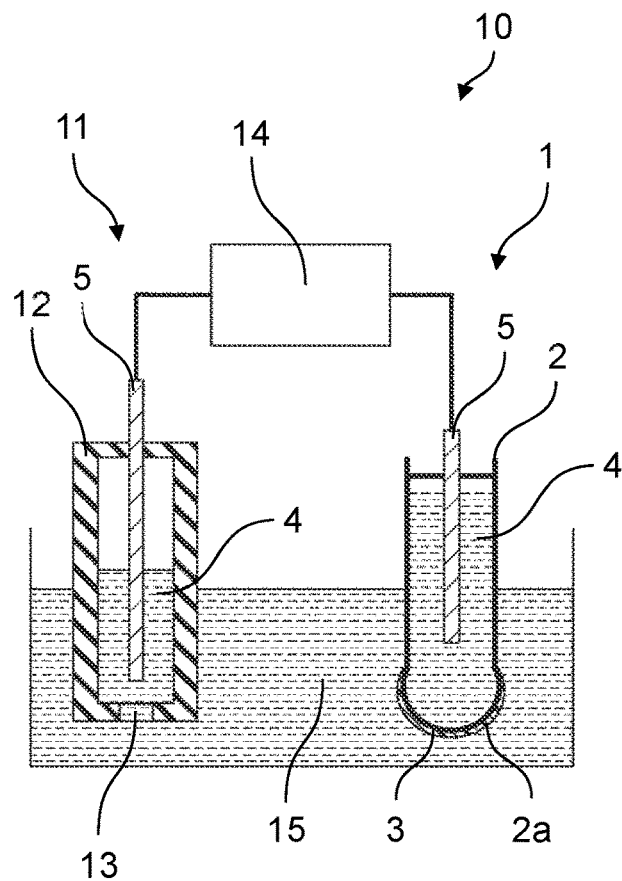
FIG. 5 is a schematic cross-sectional view of a potential response measuring apparatus used in Example 17.

For Example 17 in which a glass container was used as the solid, the potential response and the retention rate were measured using potential response measuring apparatus 10 shown in FIG. 5. Ion-selective electrode 1 has the same constitution as that shown in FIG. 1. That is, ion-selective electrode 1 includes glass container 2 as a solid, in which the outer surface of bottom 2a of glass container 2 is coated with ion-sensitive layer 3, and glass container 2 is filled with electrolytic solution 4 so that conductive member 5 (silver/silver chloride electrode) and electrolytic solution 4 come into contact with each other. Reference electrode 11 includes glass electrode body 12 having liquid junction 13, and conductive member 5 (silver/silver chloride electrode), and glass electrode body 12 is filled with electrolytic solution 4 so that conductive member 5 and electrolytic solution 4 come into contact with each other. Ion-selective electrode 1 and reference electrode 11 produced in Example 17 were connected via potentiometer 14 and immersed (at this time, they were immersed so that bottom 2a was immersed in sample solution 15) in sample solution 15 to be ion-measured, and the potential difference between ion-selective electrode 1 and reference electrode 11 was measured by potentiometer 14.

Figure 6:
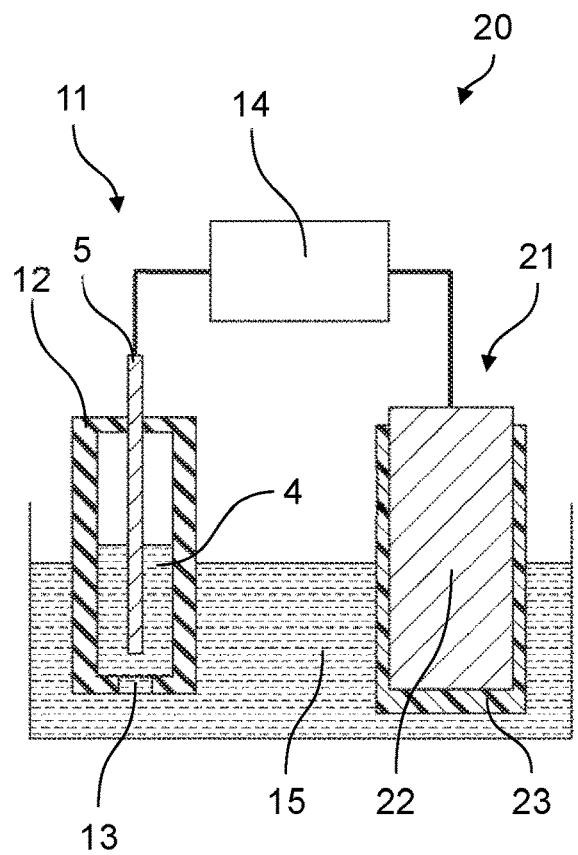
FIG. 6 is a schematic cross-sectional view of a potential response measuring apparatus used in Examples 1 to 16 and 18 to 21.

For Examples 1 to 16 and 18 to 21 in which a copper plate and a glassy carbon plate were used as solids, the potential response and the retention rate were measured using potential response measuring apparatus 20 shown in FIG. 6. As shown in FIG. 6, in ion-selective electrode 21, the surface of solid 22 is surface-coated with ion-sensitive layer 23. Reference electrode 11 is the same as that shown in FIG. 5. Ion-selective electrode 21 and reference electrode 11 produced in Examples 1 to 16 and 18 to 21 were connected via potentiometer 14 and immersed (at this time, they were immersed so that a portion of ion-selective electrode 21 not coated with ion-sensitive layer 23 (that is, a portion at which the copper plate or the glassy carbon plate is exposed) was not immersed in sample solution 15) in sample solution 15 to be ion-measured, and the potential difference between ion-selective electrode 21 and reference electrode 11 was measured by potentiometer 14.

Figure 7:
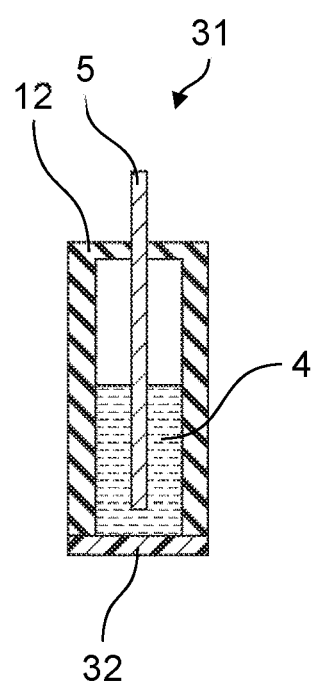
FIG. 7 is a schematic cross-sectional view of an ion-selective electrode of Comparative Example 1.

As for Comparative Example 1, one obtained by changing ion-selective electrode 1 of FIG. 5 to ion-selective electrode 31 shown in FIG. 7 was used. As shown in FIG. 7, ion-selective electrode 31 includes glass electrode body 12, ion-sensitive membrane 32 of Comparative Example 1 disposed at the bottom of glass electrode body 12, and conductive member 5 (silver/silver chloride electrode), in which glass electrode body 12 is filled with electrolytic solution 4 so that conductive member 5 and electrolytic solution 4 come into contact with each other. In this case, from the viewpoint that 2-nitrophenyl octyl ether is contained as a plasticizer in the support PVC, and bis[(12-crown-4)methyl] 2-dodecyl-2-methylmalonate, which is an ion-sensitive substance, captures sodium ions and then diffuses and moves in the plasticizer, ion-selective electrode 31 of Comparative Example 1 can be said to be a liquid membrane type ion-selective electrode (whereas ion-selective electrodes 1 and 21 of Examples 1 to 21 can be said to be a solid membrane type ion-selective electrode).

Electrolytic solution 4 was changed according to ions to be measured. That is, in Examples 1 to 12 and 15 to 20 and Comparative Example 1, a saturated aqueous solution of sodium chloride was used, in Examples 13 and 21, a saturated aqueous solution of lithium chloride was used, and in Example 14, a saturated aqueous solution of potassium chloride was used. Using sample solution 15 having a known concentration of the ions to be measured, the potential difference between the ion-selective electrode and the reference electrode was measured with potentiometer 6 while changing the concentration of the ions to be measured in sample solution 15, and a potential response was obtained. Furthermore, the potential response measurement was repeated 30 times for each of the examples and the comparative example, and the ratio (percentage) of the 30th potential response to the initial potential response was defined as the retention rate (%).

As criteria for determining the retention rate, "A" was given when the retention rate was 90% or more as a particularly excellent range, "B" was given when the retention rate was 87% or more and less than 90% as an excellent range, "C" was given when the retention rate was 85% or more and less than 87% as an acceptable range, and "D" was given when the retention rate was less than 85% as an insufficient range.

The higher the potential response, the better. As criteria for determination, "A" was given to those with a potential response of 50 mV/decade or more as a range of particularly excellent potential response, "B" was given to those with a potential response of 40 mV/decade or more and less than 50 mV/decade as a range of excellent potential response, "C" was given to those with a potential response of 35 mV/decade or more and less than 40 mV/decade as a range of acceptable potential response, and "D" was given to those with a potential response of less than 35 mV/decade as a range of insufficient potential response.

Elastic Modulus

In each of the examples, the produced solution after the first standing or heating was poured into a cylindrical mold made of polytetrafluoroethylene and heated at 80° C. for 24 hours. The size of the mold was 40 mm in diameter and 0.5 mm in depth. A strip-shaped sample of 5 mm×30 mm was cut out from the film-like solid obtained after heating for 24 hours, and the elastic modulus was measured using a known tensile strength measuring device.

Those exhibiting a high elastic modulus thought to have more siloxane bonds formed in the ion-sensitive layer, and can be said to have high strength. Furthermore, it is thought that the solution of the examples showing a high elastic modulus contains a large amount of bond species (alkoxy groups) that contribute to the siloxane bond, and it is thought that bonding (chemisorption) to the solid surface is easy and adhesiveness is easily secured. On the other hand, when the elastic modulus is too high, cracks may occur in the ion-sensitive layer.

In order to inhibit the occurrence of cracks while securing the strength of the ion-sensitive layer and the adhesiveness between the ion-sensitive layer and the solid surface, A was given to those with 110 MPa or more and 350 MPa or less as a particularly preferred elastic modulus range, B was given to those with 95 MPa or more and less than 110 MPa or more than 350 MPa and 500 MPa or less as a preferred elastic modulus range, C was given to those with 70 MPa or more and less than 95 MPa or more than 500 MPa and 650 MPa or less as an acceptable range, and D was given to those with less than 70 MPa or more than 650 MPa as a defective elastic modulus range.

The results are shown in FIGS. 8 and 9. From the results of FIGS. 8 and 9, it can be considered as follows. All of Examples 1 to 21 are examples that satisfy all of the requirements specified in the exemplary embodiments of the present disclosure, and showed sufficient retention rates (that is, "C", "B", or "A" in the determination columns of retention rates of FIGS. 8 and 9). In particular, Examples 1 to 19 and 21 showed a particularly excellent retention rate because R2 satisfied the preferred range (0.9 or less).

In Examples 1 to 18, 20, and 21, the potential response was excellent because R1 was in a preferred range (0.9 or less). Unlike Examples 1, 4 to 9, 17, 18, and 20, in Examples 2, 3, 10 to 16, and 21, the potential response was particularly excellent because R1 was in a more preferred range (0.2 or more and 0.5 or less).

In Examples 1 to 19 and 21, the elastic modulus was in a preferred range because R2 was in a preferred range (0.9 or less). Unlike Examples 1, 4 to 6, 8, 9, 17 to 19, and 21, in Examples 2, 3, 7, and 10 to 16, the elastic modulus was in a particularly preferred range because R2 was in a more preferred range (0.2 or more and 0.5 or less).

On the other hand, Comparative Example 1 is an example in which the requirements specified in the exemplary embodiment of the present disclosure were not satisfied, and the retention rate was insufficient. It is thought that, in Comparative Example 1, although the ion-selective electrode is an ion-selective electrode in which the ion-sensitive substance has the cyclic structure, presumably, the ion-sensitive substance was lost during repeated measurements, resulting in a decrease in the retention rate.

The ion-selective electrode according to the exemplary embodiment of the present disclosure has a high industrial utility value because it can be used, for example, for measuring the activity of ions dissolved in a liquid and exhibits sufficient durability at least for repeated measurement.

What is claimed is:

1. An ion-selective electrode comprising:
    an ion-sensitive layer containing an ion-sensitive substance; and
    a solid,
    wherein at least a part of a surface of the solid is coated with the ion-sensitive layer,
    the ion-sensitive substance has a crown ether structure formed of at least two or more repeating units represented by Formula (a):

    $$-CR^1R^2-CR^3X-O- \tag{a}$$

where X is an organic group having an alkoxysilyl group at a terminal, $R^1$, $R^2$, and $R^3$ are each a hydrogen atom or a hydrocarbon group, and $R^1$ or $R^2$ may be bonded to X,
    at least one of the alkoxysilyl groups of the crown ether structure reacts to be bonded to at least a part of the surface of the solid,
    the ion-sensitive layer contains a portion derived from a second compound represented by Formula (c):

    $$R^4-Z \tag{c}$$

where $R^4$ is a monovalent hydrocarbon group, and Z is a monovalent organic group having an alkoxysilyl group at a terminal, and
    a ratio of a molar number of a portion derived from the second compound to a sum of a molar number of a portion derived from a portion represented by Formula (a) and a molar number of a portion derived from the second compound is 0.9 or less.

2. The ion-selective electrode of claim 1, wherein
    the crown ether structure is a polymer containing a portion derived from a first compound having an epoxy group and an alkoxysilyl group at a terminal, and
    the polymer is obtained by cyclically polymerizing the epoxy group by ring-opening with an alkali metal salt or a salt of a group 2 element.

3. The ion-selective electrode of claim 2, wherein
a cation of the alkali metal salt or the salt of the group 2 element is any of lithium ion, sodium ion, and potassium ion.

4. The ion-selective electrode of claim 1, wherein
in Formula (a), $R^1$, $R^2$, and $R^3$ are each a hydrogen atom, and X is represented by Formula (b):

$$-CH_2O-Y \tag{b}$$

where Y is a monovalent organic group having an alkoxysilyl group at a terminal.

5. The ion-selective electrode of claim 1, wherein
the number of repetitions of Formula (a) is 10 or less.

6. The ion-selective electrode of claim 1, wherein
at least one of the alkoxysilyl groups of the crown ether structure reacts to form a siloxane bond.

7. The ion-selective electrode of claim 1, wherein
a siloxane bond is formed from a portion derived from the alkoxysilyl group in the crown ether structure and a portion derived from the alkoxysilyl group of the second compound.

8. The ion-selective electrode of claim 1, wherein
a ratio of a sum of a molar number of a portion derived from a portion represented by Formula (a) in which the number of alkoxy groups in X of Formula (a) is 3 and a molar number of a portion derived from the second compound in which the number of alkoxy groups in Z of Formula (c) is 3 to a sum of a molar number of a portion derived from a portion represented by Formula (a) and a molar number of a portion derived from the second compound is 0.9 or less.

9. The ion-selective electrode of claim 1, wherein
the solid contains a conductive material.

10. The ion-selective electrode of claim 1, wherein
the solid is a glass container,
the surface of the solid is an outer surface of the glass container, and
the ion-selective electrode further comprises:
a conductive member so that the conductive member comes into contact with an electrolytic solution when the glass container is filled with the electrolytic solution.

11. An ion-selective electrode comprising:
an ion-sensitive layer containing an ion-sensitive substance; and
a solid,
wherein at least a part of a surface of the solid is coated with the ion-sensitive layer,
the ion-sensitive substance has a crown ether structure formed of at least two or more repeating units represented by Formula (a):

$$-CR^1R^2-CR^3X-O- \tag{a}$$

where X is an organic group having an alkoxysilyl group at a terminal, $R^1$, $R^2$, and $R^3$ are each a hydrogen atom or a hydrocarbon group, and $R^1$ or $R^2$ may be bonded to X,
at least one of the alkoxysilyl groups of the crown ether structure reacts to be bonded to at least a part of the surface of the solid,
the ion-sensitive layer contains a portion derived from a second compound represented by Formula (c):

$$R^4-Z \tag{c}$$

where $R^4$ is a monovalent hydrocarbon group, and Z is a monovalent organic group having an alkoxysilyl group at a terminal, and
a ratio of a sum of a molar number of a portion derived from a portion represented by Formula (a) in which the number of alkoxy groups in X of Formula (a) is 3 and a molar number of a portion derived from the second compound in which the number of alkoxy groups in Z of Formula (c) is 3 to a sum of a molar number of a portion derived from a portion represented by Formula (a) and a molar number of a portion derived from the second compound is 0.9 or less.

* * * * *